(12) United States Patent
Grappiolo et al.

(10) Patent No.: US 9,763,790 B2
(45) Date of Patent: Sep. 19, 2017

(54) FEMORAL NECK PROSTHESIS (75) Inventors: Guido Grappiolo, Finale Ligure (IT); Roland Willi, Neftenbach (CH)

(73) Assignee: Zimmer GmbH, Winterthur (CH)

( * ) Notice: Subject to any disclaimer, the term of this patent is extended or adjusted under 35 U.S.C. 154(b) by 1530 days.

(21) Appl. No.: 11/915,251

(22) PCT Filed: May 24, 2006

(86) PCT No.: PCT/EP2006/004976
§ 371 (c)(1),
(2), (4) Date: Nov. 26, 2008

(87) PCT Pub. No.: WO2006/125633
PCT Pub. Date: Nov. 30, 2006

(65) Prior Publication Data
US 2009/0076619 A1  Mar. 19, 2009

(30) Foreign Application Priority Data
May 24, 2005  (EP) .................................. 05011259

(51) Int. Cl.
*A61F 2/36* (2006.01)
*A61B 17/88* (2006.01)
(Continued)

(52) U.S. Cl.
CPC ........ *A61F 2/3601* (2013.01); *A61B 17/8808* (2013.01); *A61B 17/8875* (2013.01);
(Continued)

(58) Field of Classification Search
CPC ............. A61B 17/8875; A61B 17/8808; A61F 2/3601; A61F 2/4607
(Continued)

(56) References Cited

U.S. PATENT DOCUMENTS 2,682,265 A    6/1954  Collison
4,908,032 A *  3/1990  Keller .................. 623/23.45
(Continued)

FOREIGN PATENT DOCUMENTS

EP    0418301 B1   10/1994
EP    1120096 A1    8/2001
(Continued)

OTHER PUBLICATIONS

"Canadian Application Serial No. 2,609,424, Office Action mailed Jan. 17, 2013", 2 pgs.

*Primary Examiner* — Corrine McDermott
*Assistant Examiner* — Joshua Levine
(74) *Attorney, Agent, or Firm* — Schwegman Lundberg & Woessner, P.A.

(57) ABSTRACT

The invention relates to a shaft for a femoral neck prosthesis, which comprises an anchoring area (27, 29) which is arranged inside the femur in order to anchor the prosthesis into bone, a head area which is axially adjacent to the anchoring area (27, 29) on the proximal side, said head area comprising a device (13) which is connected to the prosthesis head (15), in addition to a distal end which is arranged opposite the head area in the axial direction of the anchoring area (27, 29). The invention is characterised in that the maximum cross-sectional dimension of the head area is at the most equal and, in particular, smaller than the maximum diameter of the anchoring area (27, 29), in such a manner that the maximum cross-sectional dimension of the shaft (11) is in the anchoring area (27, 29).

44 Claims, 9 Drawing Sheets

(51) Int. Cl.
*A61F 2/46* (2006.01)
*A61B 17/74* (2006.01)
*A61F 2/30* (2006.01)

(52) U.S. Cl.
CPC .......... *A61F 2/4607* (2013.01); *A61B 17/742* (2013.01); *A61F 2002/30062* (2013.01); *A61F 2002/3085* (2013.01); *A61F 2002/30179* (2013.01); *A61F 2002/30331* (2013.01); *A61F 2002/30332* (2013.01); *A61F 2002/30474* (2013.01); *A61F 2002/30604* (2013.01); *A61F 2002/30827* (2013.01); *A61F 2002/30878* (2013.01); *A61F 2002/365* (2013.01); *A61F 2002/3611* (2013.01); *A61F 2002/4631* (2013.01); *A61F 2002/4636* (2013.01); *A61F 2210/0004* (2013.01); *A61F 2220/0025* (2013.01); *A61F 2220/0033* (2013.01); *A61F 2230/0058* (2013.01)

(58) Field of Classification Search
USPC ......... 623/22.41–22.46, 23.15, 23.18, 23.19, 623/23.26, 23.27
See application file for complete search history.

(56) References Cited

U.S. PATENT DOCUMENTS

| | | | |
|---|---|---|---|
| 4,946,461 A | 8/1990 | Fischer | |
| 4,976,740 A | 12/1990 | Kleiner | |
| 5,370,662 A | 12/1994 | Stone et al. | |
| 5,580,352 A * | 12/1996 | Sekel | 623/22.46 |
| 5,702,479 A * | 12/1997 | Schawalder | 623/23.15 |
| 5,800,553 A | 9/1998 | Albrektsson et al. | |
| 5,980,170 A | 11/1999 | Salyer | |
| 5,980,575 A | 11/1999 | Albrektsson et al. | |
| 6,162,227 A | 12/2000 | Eckhardt et al. | |
| 6,245,111 B1 | 6/2001 | Shaffner | |
| 6,273,915 B1 | 8/2001 | Grimes | |
| 6,284,002 B1 | 9/2001 | Sotereanos | |
| 6,375,684 B1 | 4/2002 | Kriek | |
| 6,383,227 B1 | 5/2002 | Baroud et al. | |
| 6,824,568 B1 * | 11/2004 | Albrektsson | A61F 2/3601 623/23.15 |
| 7,261,716 B2 | 8/2007 | Strobel et al. | |
| 2003/0050704 A1 | 3/2003 | Keynan | |
| 2003/0130741 A1 | 7/2003 | McMinn | |
| 2003/0163202 A1 | 8/2003 | Lakin | |
| 2005/0015153 A1 * | 1/2005 | Goble et al. | 623/23.46 |
| 2006/0135960 A1 | 6/2006 | Munro et al. | |

FOREIGN PATENT DOCUMENTS

| | | |
|---|---|---|
| GB | 2372707 A | 9/2002 |
| JP | 3-504932 A | 10/1991 |
| JP | 3311748 B2 | 12/1993 |
| JP | 7-504104 A | 5/1995 |
| JP | 2001-511038 A | 8/2001 |
| JP | 2003-038509 A | 2/2003 |
| WO | WO89/11837 A1 | 12/1989 |
| WO | WO93/16663 A1 | 9/1993 |
| WO | WO98/34567 A1 | 8/1998 |
| WO | WO00/09044 A1 | 2/2000 |
| WO | WO2004/098425 A2 | 11/2004 |

* cited by examiner

FEMORAL NECK PROSTHESIS

This application is a U.S. National Phase Patent Application based on International Application Serial No. PCT/EP2006/004976 filed May 24, 2006, the disclosure of which is hereby explicitly incorporated by reference herein.

The invention relates to a femoral neck prosthesis comprising an anchorage region provided for arrangement in the interior of the femur for the anchorage of the prosthesis in the bone, a head region which adjoins the anchorage region axially at a proximal side and has a device for connection to a prosthesis head, and a distal end which is disposed opposite the head region in the axial direction of the anchorage region.

Hip joint prostheses are generally known, for example from WO 00/09044 A1, in which the prosthesis shaft does not extend into the femur shaft (corpus femoris) as with shaft-fixed prostheses, but rather extends through the neck of the femur (collum femoris) without anchorage in the femur shaft. Prostheses of this type are also known as femoral neck prostheses.

A shaft of the initially named kind should be set forth which can be anchored to the femur in as simple and as secure a manner as possible. The shaft set forth in claim 1 can satisfy this demand in addition to a plurality of further advantageous properties.

Provision is made with the shaft set forth here for the maximum cross-sectional dimension of the head region to be at most the same size as, and in particular smaller than, a maximum diameter of the anchorage region such that the maximum cross-sectional dimension of the shaft is present in the anchorage region. The anchorage of the shaft can take place inside a passage formed in the femur due to the anchorage region. In contrast to known thrust plate prostheses in which the prosthesis is supported axially at the resection surface via a plate-like element, with the implant set forth here, the fixing takes place within a bore extending substantially in the axis of the neck through the femur. It in particular proves to be favorable that, since no region is present at proximal whose cross-sectional dimension is larger than in the anchorage section, the insertion of the prosthesis can take place by minimally invasive techniques and in particular from lateral. When the anchorage region has an external thread section, the thread flanks can be provided with a height which is sufficient for a secure hold and simultaneously ensures a non-critical strain on the cortex.

Further embodiments are set forth in the dependent claims, in the description as well as in the drawing, with the features of these embodiments being able to be combined with one another in any desired manner per se.

The anchorage region of the shaft can include a cementing section and an external thread section with a spongiosa thread. This embodiment represents a hybrid solution, with the thread substantially serving for the reception of axial forces and the cementing section substantially serving for the support of torques. The thread is bearing in the femoral neck region where the cortex or the relatively compact spongiosa are located. A rather low tissue density and tissue strength is present in the transition region between the trochanter and the femoral neck. The prosthesis is supported in this region, with the bone cement stabilizing the spongiosa having a relatively low density. The introduction of the bone cement can take place by pressing in. The cementing section can, for example, have at least one recess for the reception of bone cement at its outer periphery.

The cementing section can furthermore have a geometry which is cross-shaped or star-shaped in cross-section in at least one axial region, with substantially axially extending recesses being formed. Such a cross configuration or star configuration is also suitable for the use of instruments for screwing in or manipulating from lateral. The recesses can extend up to the distal end of the cementing section. Provision can also be made for the cementing section to have at least one spirally or annularly circumferential groove as a recess for the reception of bone cement.

The recess can be accessible from the distal end of the shaft. This facilitates the handling from lateral on implanting.

The shaft has means in an exemplary embodiment which ensure a fluid communication for the supply of bone cement from the distal end of the shaft to the recess, which likewise facilitates the handling.

The external thread section can be arranged adjacent to the head region. It thus comes to lie in a region in which the thread comes to lie in spongiosa with a comparatively high density and finds a hold in the cortex at best with the thread tips.

The spongiosa thread, for example, has a substantially constant core diameter and/or a substantially constant external diameter. The maximum diameter of the external thread defines the maximum diameter of the shaft in an embodiment of the described implant. The thread height amounts in this context to at least 3 mm, and in particular at least 4.5 mm, in specific embodiments.

Provision can furthermore be made for the maximum cross-sectional dimension of the head region to exceed the maximum core diameter of the thread by a maximum of ⅓ of the difference between the maximum external diameter and the maximum core diameter of the thread, and is in particular at most the same size as the maximum core diameter of the thread. This makes it possible that the shaft can be inserted from lateral via an opening provided for the reception of the anchorage region.

If the shaft has a cementing section, it can, for example, adjoin the threaded section at distal and thus permit a support in the spongiosa which has good cement support.

The maximum cross-sectional dimension of the cementing section exceeds the maximum core diameter of the thread in an embodiment by at most ⅓ of the difference between the maximum external diameter and the maximum core diameter of the thread and is in particular at most the same size as the maximum core diameter of the thread. Provision can furthermore be made for the maximum cross-sectional dimension of the cementing section to be at least as large as the maximum cross-sectional dimension of the head region. These optional features ensure a good fit of the cementing section in the bore established for the insertion of the implant.

The cementing section can be provided with a sealing section in the region of its distal end, with the sealing section being made in thread form for example. If the anchorage region includes an external thread section with a spongiosa thread, the thread-shaped sealing section can correspond to the spongiosa thread, in particular with respect to the dimension of the external diameter and/or of the thread height.

The head section and the anchorage section are arranged coaxially, for example. A coaxial arrangement can likewise be present between at least two of the regions or sections head region, cementing section and external thread section.

The proximal to distal extent of the anchorage region can be dimensioned such that the distal end of the shaft comes to lie in the spongiosa tissue of the femur. The shaft then does not project laterally out of the femur.

The head region, for example, has a conical or truncated conical connection element for connection to a prosthesis head.

An instrument set is also set forth here with which the shaft can be anchored to the femur in a simple and secure manner and the femoral neck prosthesis including the shaft can thus likewise be inserted in a simple and secure manner. The instrument set includes a trepanning drill and a thread cutter for the manufacture of a passage as well as a screwing instrument to screw the shaft into the passage from lateral. An introduction instrument can additionally be provided for the introduction of bone cement which has an introduction section which can be mounted onto the distal end of the shaft. The introduction section can be made in the manner of a grommet and serves in particular as an adapter for the optimum adaptation of the outflow end of a conventional cement syringe or cement gun to the distal end of the prosthesis shaft. The introduction section can be calibrated to the distal end of the shaft such that, in the mounted state, a channel formed in the shaft is sealed with respect to the environment. The introduction section can in particular be made in cap-shape, hood-shape or bell-shape at least regionally. The introduction section can be a separate component which can be connected to a cement syringe or cement gun.

The instrument set can be used in a method for the insertion of a femoral neck prosthesis of the kind described above in which the femoral head is removed via a front access and a corresponding incision, a core hole extending from lateral through the neck of the femur is formed, a thread is cut into the core hole, the prosthesis shaft is screwed into the passage formed in this manner and the prosthesis head is mounted onto the shaft via the front access.

The shaft can be cemented in for example, provided a cementing section is provided. The bone cement is in particular introduced with a shaft already located in the passage. An in particular grommet-like introduction section of an introduction instrument can be mounted on to the distal end of the shaft for the cementing in thereof.

The machining of the acetabulum (hip ball-and-socket joint) of the hip bone for the insertion of the prosthesis shell in particular takes place via the front access (anterior) via which the femoral head is previously removed. Alternatively, it is also possible to carry out this machining via the previously formed core hole or the finished passage. In this process, a sleeve can be pushed into the core hole or into the finished passage through which subsequently spindles for the necessary machining instruments can be guided and the actual instruments can be plugged onto the spindles pushed through. This sleeve can be utilized for the fixing of the femur in that the femur is fixed via an outwardly projecting section of the sleeve in a position correctly aligned relative to the hip bone, in particular on the operating table. The prosthesis shell can in particular be inserted via the front access via which the femoral head is removed, with this being able to take place after the forming of the core hole and before the cutting of the thread.

An anchorage of the prosthesis shaft by means of a thread formed in the passage makes it possible that a proximal-to-distal positional correction can be carried out by rotation of the shaft in the passage, with this being able to take place after the mounting of the prosthesis head.

All indications of alignment, positioning, orientation and direction which are used as required both in the claims and in the description as well as in the drawings in connection with the prosthesis and in accordance with the technically usual conventions and which in particular relate to anatomical axes, planes, directions in space and directions of movement are familiar to the person skilled in the art and relate to the implanted state of the prosthesis.

The invention will be described in the following by way of example with reference to the drawing. There are shown.

Figure 1A:
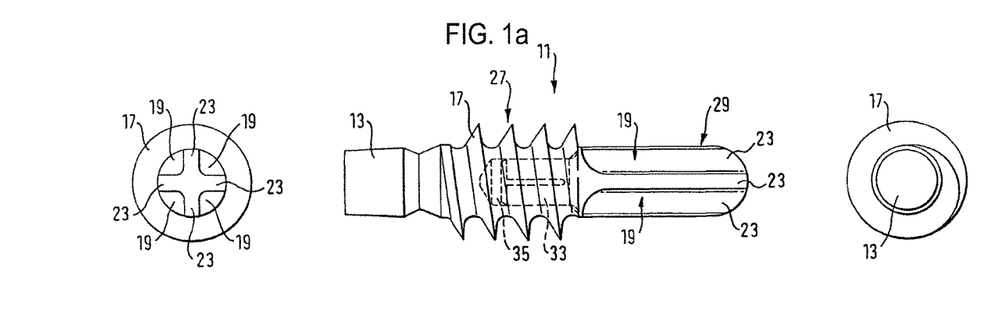
FIG. 1a different views of a prosthesis shaft of a hip joint prosthesis in accordance with a first embodiment.

Only the prosthesis shaft 11 of the hip joint prosthesis in accordance with the first embodiment is shown in FIG. 1a. The shaft 11 is made in multiple parts and includes a distal cementing section 29 and a proximal section, which is also called a head section and which is made at the proximal end as a cone 13 as well as a section 27 adjoining the cone 13 toward distal and provided with an external thread 17 made as a spongiosa thread. The cone 13 serves for the coupling to a prosthesis head not shown here and having a correspondingly shaped mount for the cone 13. The prosthesis furthermore includes a joint shell, likewise not shown, for the insertion into the hip bone. The two shaft parts 27, 29 described are firmly plugged together to form the shaft 11. For this purpose, the cementing section 29 is provided with a connection spigot 33 for which a corresponding spigot mount 35 is formed in the threaded section 27. The cementing section 29 has a star-shaped cross-section which is formed by four webs 23 standing at right angles to one another in respective pairs, extending in the axial direction and bounding recesses 19 for the reception of bone cement in the peripheral direction which are elongated in axial direction and open to distal.

Figure 1B:
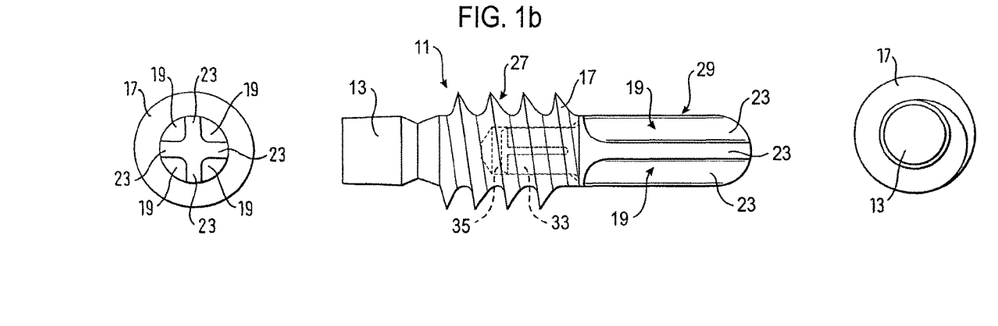
FIG. 1b views in accordance with FIG. 1a of a prosthesis shaft in accordance with a second embodiment.

FIG. 1b shows a second embodiment which differs from the first embodiment (FIG. 1a) by the configuration of the spongiosa thread 17. The arrangement of the thread flanks in the second embodiment is reversed relative to the first embodiment with respect to the axial direction.

Figure 2:
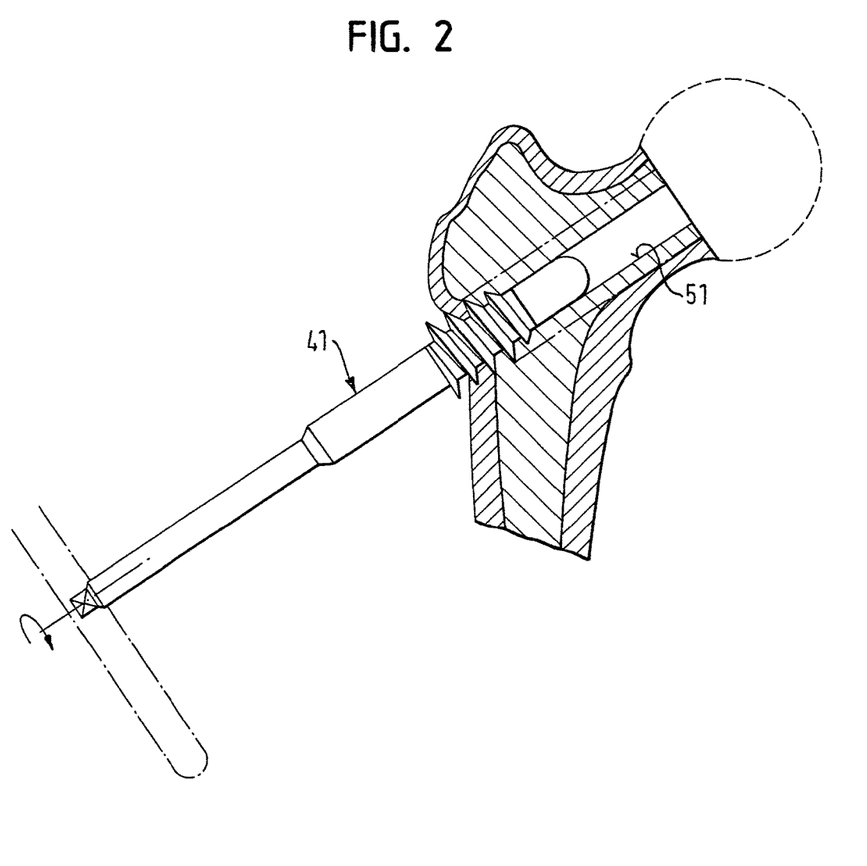
FIG. 2 a thread cutter of a set of instruments.

FIG. 2 shows how a thread is cut on the femur into a previously formed core hole 51 by means of a thread cutter 41 in extension of the axis of the neck of the femur coming from lateral. The femoral head is only shown by dashed lines since is has already been removed in this phase of the surgical procedure which will be looked at in more detail in the following.

Figure 3:
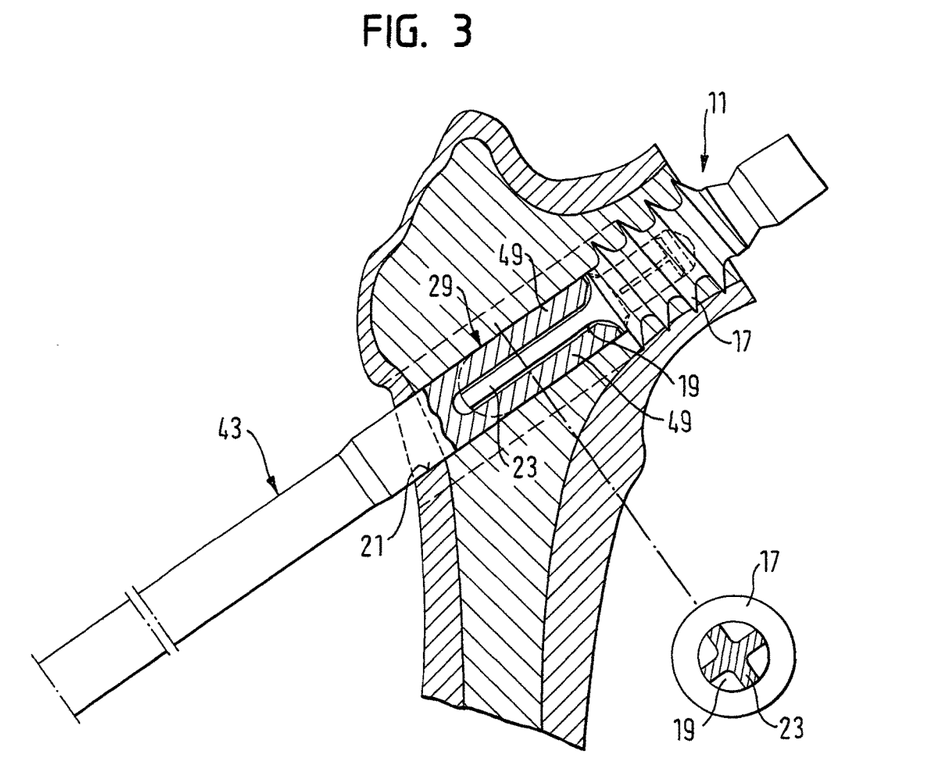
FIG. 3 the screwing in of the prosthesis shaft of the first embodiment with a screwing instrument.

In accordance with FIG. 3, the set of instruments furthermore includes a screwing instrument 43 which is calibrated to the distal cementing section 29 of the prosthesis shaft 11. The screwing instrument 43 is provided with fingers 49 which engage into the recesses 19 of the cementing section

29. The screwing instrument 43 is formed in this respect in a complementary manner to the cementing section 29 of the shaft 11.

Figure 4:
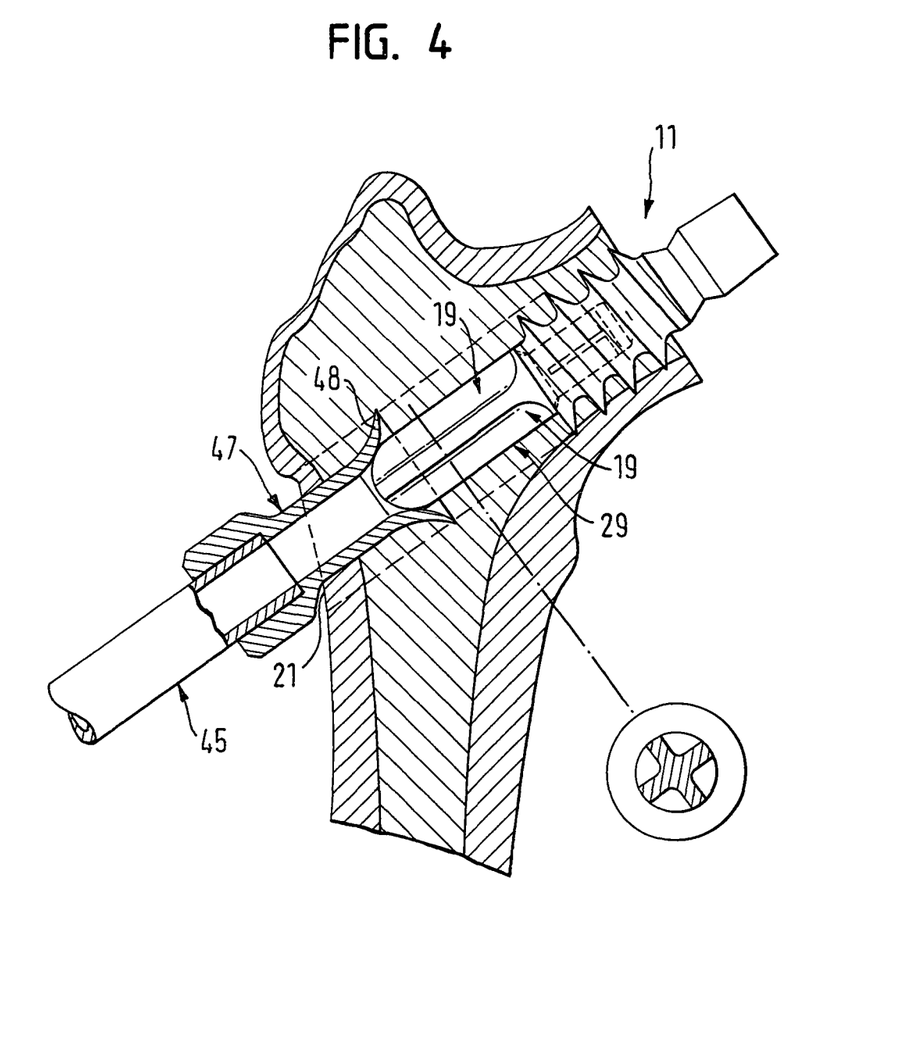
FIG. 4 the introduction of bone cement with a prosthesis shaft of the first embodiment with an introduction instrument.

In accordance with FIG. 4, an introduction instrument 45 of the set of instruments, which includes an introduction section 47 matched to the shape of the rear end of the cementing section 29, serves for the cementing in of the prosthesis shaft 11. The introduction section 47 is provided as a separate component which can be mounted on a conventional cement syringe or cement gun and thus serves as a type of adapter grommet. The discharge region of the introduction section 47 is made as a bell-shaped contact region 48 which projects radially beyond the cementing section 29 having only the core hole diameter and supports a radial widened section of the injected bone cement by its shape and prevents a discharge of bone cement from the passage 21. The injected bone cement enters via the introduction section 48 into the recesses 19 of the cementing section 29 and from there in substantially a radial direction into the material of the spongiosa of the femur bone with open pores.

Figure 5:
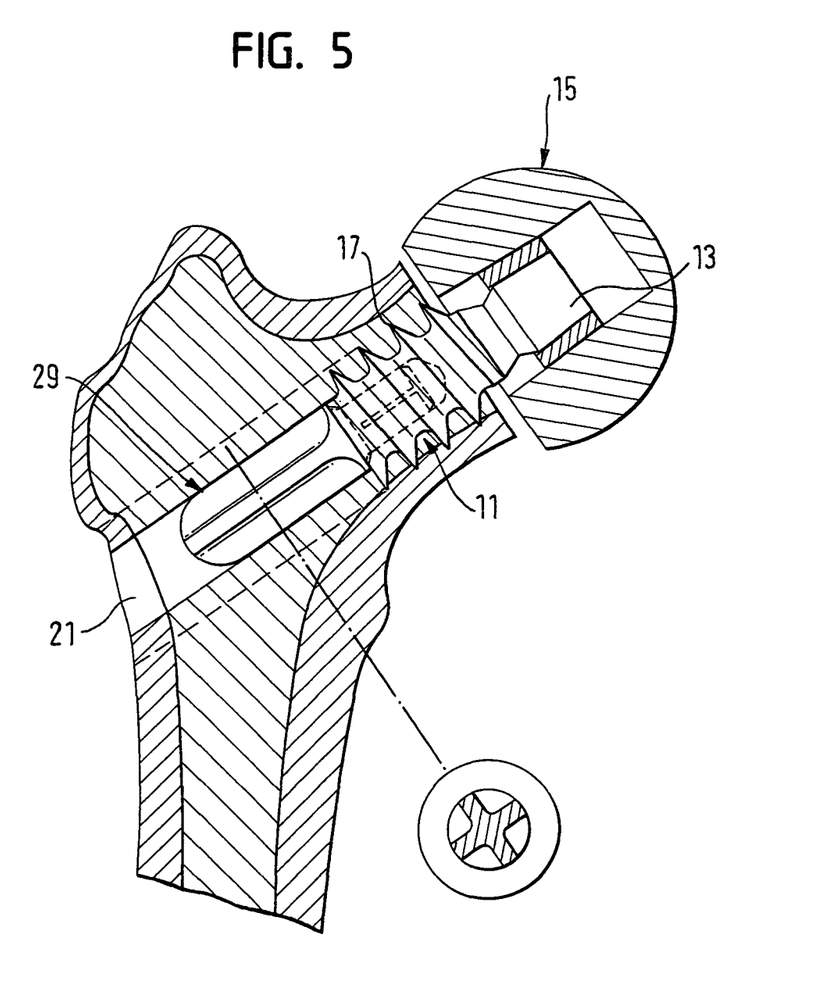
FIG. 5 a prosthesis shaft of the first embodiment in the inserted state with a mounted prosthesis head.

In the completed state in accordance with FIG. 5, the prosthesis shaft 11 provided with the prosthesis head 15 mounted on the cone 13 is located in the correct depth inside the passage 21 and is anchored in the relatively hard region of the neck of the femur via the proximal thread 17 and in the relatively open-pored spongiosa via the cementing section 29 at the femur. The prosthesis shaft 11 is thus fixed in the femur practically over its total axial length without external pressing devices or clamping devices being necessary to fasten the prosthesis shaft 11.

Figure 6:
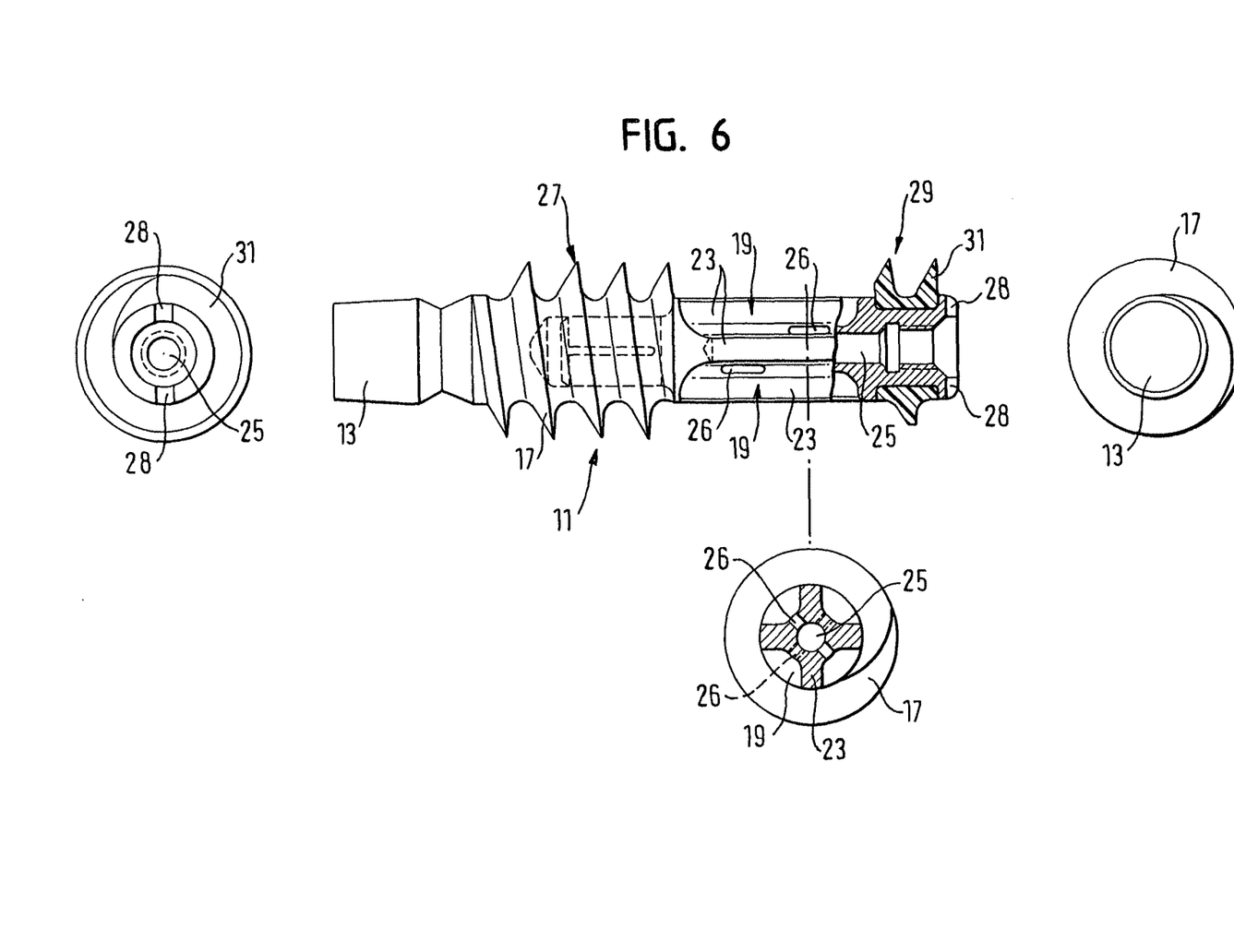
FIG. 6 different views of a prosthesis shaft of a hip joint prosthesis in accordance with a third embodiment.
Figure 7:
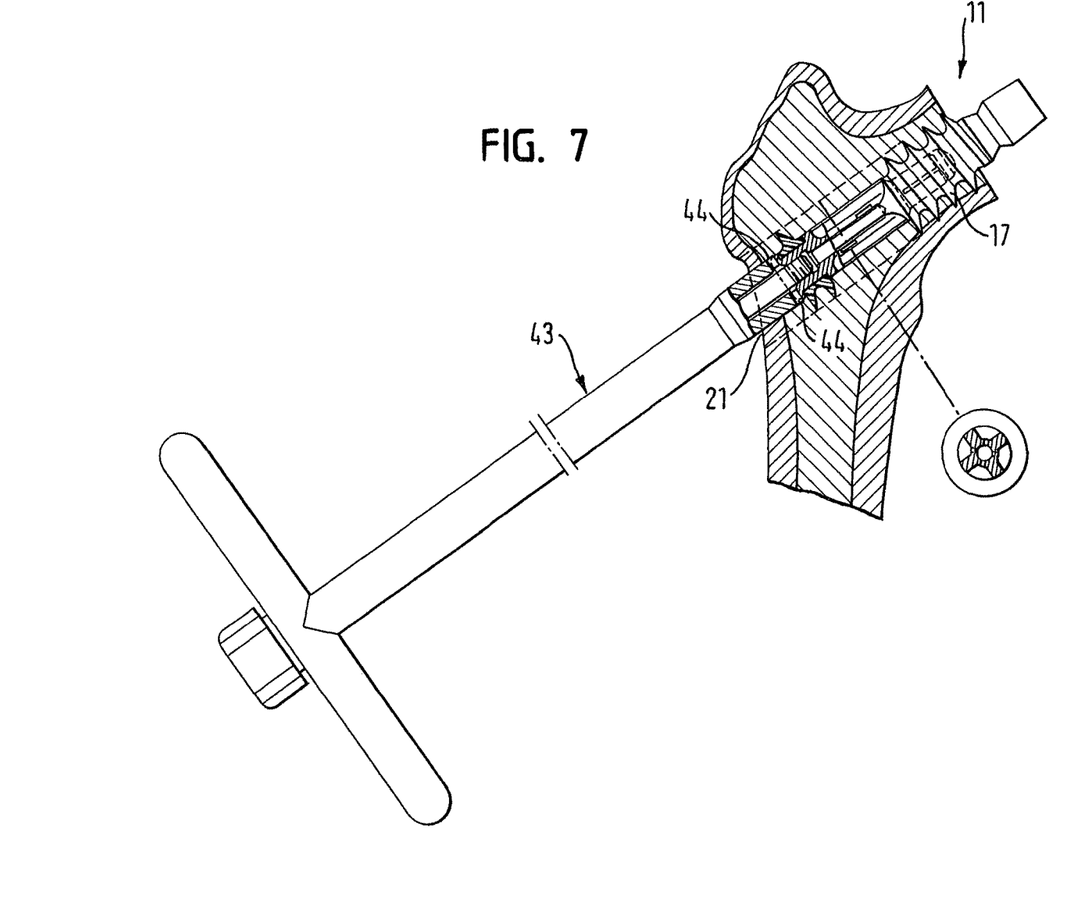
FIG. 7 the screwing in of the prosthesis shaft of the third embodiment with another screwing instrument.
Figure 8:
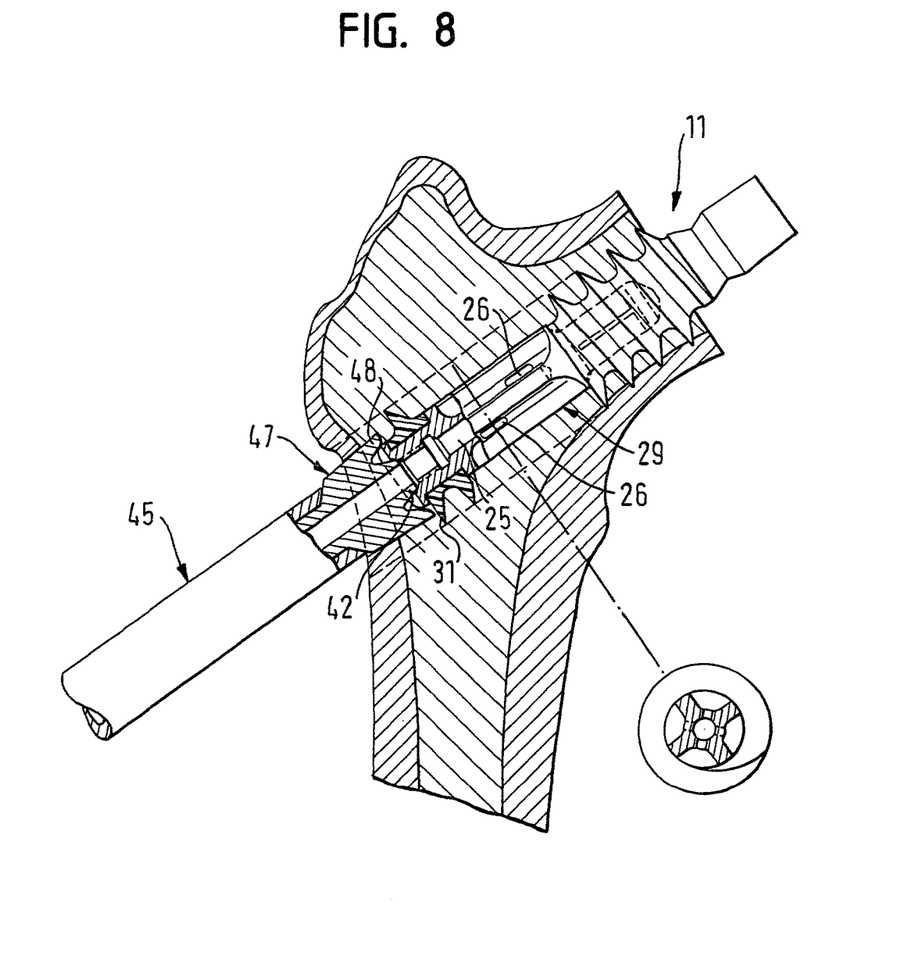
FIG. 8 the introduction of bone cement with a prosthesis shaft of the third embodiment with another introduction instrument.

The third embodiment of a prosthesis shaft 11 shown in FIG. 6 differs from the two previously described embodiments by the design of the cementing section 29. The recesses 19 which are in turn provided and extend in the axial direction between web-like wall sections 23 are not open to distal here and are not directly filled with bone cement. The cementing section 29 is rather provided with an axially extending, central introduction channel 25 which is accessible from distal and communicates with the recesses 19 via radial openings 26. These openings 26 are arranged offset to one another with respect to the axial direction. In the region of its distal end, the cementing section 29 is provided with a threaded section 31 which serves as a seal on the introduction of the bone cement, as will be looked at in more detail in the following. The threaded section 31 is calibrated to the proximal anchorage thread 17 and is in particular designed as its prolongation. Since the primary purpose of the threaded section 31 is not the anchorage of the shaft 11 in the femur bone, the threaded section 31 can e.g. be made from a bioabsorbable material. The distal end face of the cementing section 29 is provided with two cut-outs 28 diametrically opposed to one another. As FIG. 7 shows, these cut-outs 28 serve for the reception of correspondingly shaped projections 44 of a screwing instrument 43 with which the shaft 11 is screwed into the previously manufactured passage 21 in the femur bone. Not only this screwing instrument 43, but also the instrument 45 for the introduction of bone cement differs from the corresponding instrument for the first and second embodiments. As FIG. 8 shows, the contact region 48 of the grommet 47 sealing the distal end of the cementing section 29 in the mounted state has a radial inner ring wall 42, which outwardly seals the channel 25 of the cementing section 29, in addition to a radially outer ring wall which outwardly encompasses the distal end of the cementing section 29. Unlike the introduction instrument for the first and second embodiments of the prosthesis shaft, the radially outer ring wall of the contact region 48 does not have any guidance or sealing function in the introduction instrument 45 shown in FIG. 8. The axially extending channel 25 and the openings 26 opening into the recesses 19 provide a radial outflow of the bone cement from the recesses 19. The sealing of the passage 21 is ensured by the seal 31 made as a thread.

Figure 9:
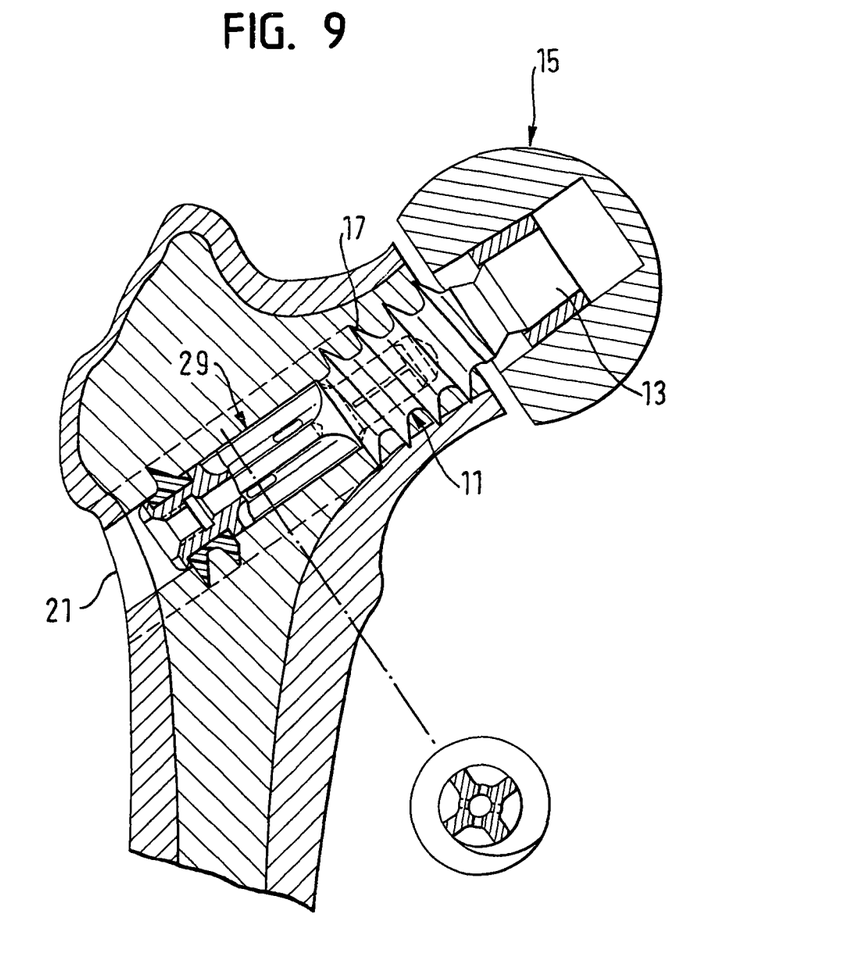
FIG. 9 a prosthesis shaft of the third embodiment in the inserted state with mounted prosthesis head.

The prosthesis shaft 11 of the third embodiment in accordance with FIG. 9 is thus also anchored reliably at the femur bone via the thread 17 in the comparatively hard material of the neck of the femur and via the bone cement cooperating with the cementing section 29 in the comparatively open-pored material of the spongiosa.

Irrespective of which cementing section 29 is used for the prosthesis shaft 11, the routine of the surgical procedure for the insertion of the prosthesis is as follows:

First, the femoral head is cut off and removed via a front access (anterior). Then either the acetabulum of the hip bone is immediately machined, and indeed likewise through the mentioned front access, or the trepanning bore 51 (cf. e.g. FIG. 2) anyway required is first established. This is done with the help of a computer-aided optical navigation system. For the machining of the acetabulum via the trepanning bore 51, a machining sleeve (not shown) is pushed into the latter and the instruments required for the machining of the acetabulum can subsequently be supplied via it. The correct alignment of the femur bone relative to the hip bone required in this process can be fixed in that the machining sleeve is dimensioned such that it projects laterally out of the femur of the patient and is held at the operation table by suitable means. The subsequent insertion of the prosthesis shell (not shown) takes place in turn via the mentioned front access. Then, after removal of the machining sleeve, a throughgoing internal thread for the prosthesis shaft 11 is formed in the trepanning bore 51 by means of the thread cutter. Subsequently, the prosthesis shaft 11 is screwed into a depth previously fixed as part of the operation planning by means of the screwing instrument 43 (cf. FIG. 3 or FIG. 7). Then—again via the mentioned front access—the prosthesis head 15 is inserted and mounted onto the cone 15 of the prosthesis shaft 11. The blows onto the head 15 required for the fixing of the head 15 on the cone 13 are also carried out through the front access by means of corresponding instruments not shown here. Subsequently, the correct position of the prosthesis head 15 can be inspected and, if necessary, corrected by rotating the prosthesis shaft 11 in the passage 21. If the correct position, i.e. the correct depth of the prosthesis shaft 11 in the passage 21, has been reached, the prosthesis shaft 11 is cemented in with the aid of the introduction instrument 45 (cf. FIG. 4 or FIG. 8). For this purpose, the respective "grommet" 47, which is attached to a conventional cement syringe, is mounted onto the distal end of the prosthesis shaft 11, as was explained above. As soon as the cement has hardened, the prosthesis shaft 11 is not only reliably anchored in the femur bone via its thread 17, but also via the cementing section 29.

A property of the prosthesis set forth here comprises the fact that it is possible to work only with minimally invasive surgical procedures and that an insertion of the shaft from lateral can take place, with only the mounting of the prosthesis head having to take place from medial.

Reference Numeral List

11 shaft of the prosthesis
13 proximal end section, coupling section, cone
15 head of the prosthesis 17 thread of the prosthesis shaft, spongiosa thread
19 recess, mount
21 passage
23 wall section, web
25 channel
26 opening
27 anchorage section with thread
28 cut-out for screwing instrument
29 anchorage section with recess, cementing section
31 sealing section, rear threaded section
33 connection spigot
35 spigot mount
41 thread cutter
42 radially inner ring wall
43 screwing instrument
44 projection of the screwing instrument
45 introduction instrument, cement syringe or cement gun
47 introduction section, grommet
48 contact region
49 finger of the screwing instrument
51 trepanning bore

The invention claimed is:

1. A shaft for a femoral neck prosthesis, comprising:
an anchorage region provided for arrangement in the interior of the femur for anchorage of the femoral neck prosthesis in the femur, the anchorage region having an anchorage region axis and a maximum radial extent with respect to the anchorage region axis, the anchorage region including an external threaded section with a spongiosa thread, wherein a maximum diameter of the external threaded section defines the maximum diameter of the shaft;
a head region unitarily formed with the external threaded section and including a truncated conical connection element that is to reside outside the femur for being received in a conical bore in a femoral head prosthesis for connecting the truncated conical connection element to the femoral head prosthesis by administering blows to the femoral head prosthesis when the truncated conical connection element is received in the conical bore, the head region situated proximally of the anchorage region in an axial direction of the anchorage region and having a maximum radial extent with respect to the anchorage region axis that is no larger than the maximum radial extent of the anchorage region, the external threaded section arranged proximate the head region; and
a distal end which is disposed opposite the head region in the axial direction of the anchorage region, wherein the maximum radial extent of the anchorage region comprises a maximum radial extent of the shaft with respect to the anchorage region axis.

2. A shaft in accordance with claim 1, wherein the anchorage region includes a cementing section.

3. A shaft in accordance with claim 2, wherein the cementing section has at least one recess for the reception of bone cement at its outer periphery.

4. A shaft in accordance with claim 3, wherein the cementing section defines a cementing cross-section having a geometry of cross-shape or star shape in cross-section at least in an axial region, whereby the geometry of the cementing cross-section forms a plurality of substantially axially extending recesses.

5. A shaft in accordance with claim 4, wherein the recesses extend up to a distal end of the cementing section.

6. A shaft in accordance with claim 3, wherein the cementing section has a least one of a spiral and an annular circumferential groove which provides a recess for the reception of bone cement.

7. A shaft in accordance with claim 3, wherein the recess is accessible from the distal end of the shaft.

8. A shaft in accordance with claim 3, further comprising means for ensuring a fluid communication for a supply of bone cement from the distal end of the shaft to the recess.

9. A shaft in accordance with claim 2, wherein the cementing section adjoins the external threaded section distally.

10. A shaft in accordance with claim 2, wherein a maximum radial extent of the cementing section exceeds a maximum core diameter of the external threaded section by a maximum of ⅓ of the difference between a maximum external diameter of the external threaded section and the maximum core diameter of the external threaded section, and is at most the same size as the maximum core diameter of the external threaded section.

11. A shaft in accordance with claim 2, wherein a maximum radial extent of the cementing section is at least the same size as the maximum radial extent of the head region.

12. A shaft in accordance with claim 1, wherein the spongiosa thread has at least one of a substantially constant core diameter and a substantially constant external diameter.

13. A shaft in accordance with claim 1, wherein the external threaded section has a thread height of at least 4.5 mm.

14. A shaft in accordance with claim 1, wherein the maximum radial extent of the head region exceeds a maximum core diameter of the external threaded section by a maximum of ⅓ of the difference between a maximum external diameter of the external threaded section and the maximum core diameter of the external threaded section, and is at most the same size as the maximum core diameter of the external threaded section.

15. A shaft in accordance with claim 1, wherein the anchorage region includes a cementing section, the cementing section including a sealing section proximate a distal end of the cementing section.

16. A shaft in accordance with claim 15, wherein the sealing section is made in thread form.

17. A shaft in accordance with claim 16, wherein the thread form of the sealing section corresponds to the spongiosa thread of the external threaded section of the anchorage region with respect to at least one of the dimension of the external diameter and the thread height.

18. A shaft in accordance with claim 1, wherein the head region and the anchorage region are arranged coaxially.

19. A shaft in accordance with claim 1, wherein the anchorage region includes a cementing section, the head region and at least one of the cementing section and the external threaded section being arranged coaxially.

20. A shaft in accordance with claim 1, wherein the head region defines a head region axis and the anchorage region defines an anchorage region axis, the truncated conical connection element disposed along the head region axis, the head region axis parallel to the anchorage region axis.

21. A shaft for a femoral neck prosthesis, comprising:
an anchorage section provided for arrangement in the interior of the femur for anchorage of the femoral neck prosthesis in the femur, wherein the anchorage section includes an external threaded section with a spongiosa thread, wherein a maximum diameter of the external threaded section defines the maximum diameter of the shaft, and the anchorage section having an anchorage section axis and a maximum radial extent with respect to the anchorage section axis;
a head region including a truncated conical connection element that is to reside outside the femur for being received in a conical bore in a femoral head prosthesis for connecting the truncated conical connection element to the femoral head prosthesis by administering blows to the femoral head prosthesis when the truncated conical connection element is received in the conical bore, the head region situated proximally of the anchorage section in an axial direction of the anchorage section and having a maximum radial extent with respect to the anchorage section axis that is no larger than the maximum radial extent of the anchorage section; and
a distal end cementing section which is disposed opposite the head region in the axial direction of the anchorage section, the distal end cementing section coupled to the anchorage section with an axial segment of the cementing section received in a blind bore in the anchorage section, wherein the blind bore includes an entrance into the blind bore which occurs at a distal end of the anchorage section with the blind bore terminating distally of a proximal end of the truncated conical connection element of the head region, wherein the maximum extent of the anchorage section comprises a maximum radial extent of the shaft with respect to the anchorage section axis, the distal end cementing section sized to receive cement proximate the cementing section, the cementing section adjoining the threaded section distally.

22. A shaft in accordance with claim 21, wherein the cementing section has at least one recess for the reception of bone cement at its outer periphery.

23. A shaft in accordance with claim 22, wherein the cementing section has a geometry of cross-shape or star shape in cross-section at least in an axial region, whereby the geometry of the cementing section forms a plurality of substantially axially extending recesses.

24. A shaft in accordance with claim 23, wherein the recesses extend up to a distal end of the cementing section.

25. A shaft in accordance with claim 22, wherein the recess is accessible from the distal end of the shaft.

26. A shaft in accordance with claim 21, wherein the cementing section has at least one of a spiral and an annular circumferential groove which provides a recess for the reception of the bone cement.

27. A shaft in accordance with claim 21, further comprising means for ensuring a fluid communication for a supply of bone cement from the distal end of the shaft to the recess.

28. A shaft in accordance with claim 21, wherein the external threaded section is arranged adjacent to the head region.

29. A shaft in accordance with claim 21, wherein the spongiosa thread has at least one of a substantially constant core diameter and a substantially constant external diameter.

30. A shaft in accordance with claim 21, wherein the external threaded section has a thread height of at least 3 mm.

31. A shaft in accordance with claim 21, wherein the maximum radial extent of the head region exceeds a maximum core diameter of the external threaded section by a maximum of ⅓ of the difference between a maximum external diameter of the external threaded section and the maximum core diameter of the external threaded section, and is at most the same size as the maximum core diameter of the external threaded section.

32. A shaft in accordance with claim 21, wherein a maximum radial extent of the cementing section exceeds a maximum core diameter of the external threaded section by a maximum of ⅓ of the difference between a maximum external diameter of the external threaded section and the maximum core diameter of the external threaded section, and is at most the same size as the maximum core diameter of the external threaded section.

33. A shaft in accordance with claim 21, wherein a maximum radial extent of the cementing section is at least the same size as the maximum radial extent of the head region.

34. A shaft in accordance with claim 21, wherein the cementing section includes a sealing section proximate a distal end of the cementing section.

35. A shaft in accordance with claim 34, wherein the sealing section is made in thread form.

36. A shaft in accordance with claim 35, wherein the thread form of the sealing section corresponds to the spongiosa thread of the external threaded section of the anchorage region with respect to at least one of the dimension of the external diameter and the thread height.

37. A shaft in accordance with claim 21, wherein the head region and the anchorage region are arranged coaxially.

38. A shaft in accordance with claim 21, wherein the head region and at least one of the cementing section and the external threaded section being arranged coaxially.

39. A shaft in accordance with claim 21, wherein the proximal to distal extent of the anchorage region is dimensioned such that, when the shaft is implanted in a femoral neck, the distal end of the shaft comes to lie in the spongiosa tissue of the femur.

40. A shaft is accordance with claim 21, wherein the head region is unitarily formed with the anchorage section.

41. A shaft in accordance with claim 21, wherein the head region defines a head region axis and the anchorage region defines an anchorage region axis, the truncated conical connection element disposed along the head region axis, the head region axis parallel to the anchorage region axis.

42. A system for implanting a shaft for a femoral neck prosthesis, the system comprising:
a shaft for a femoral neck prosthesis, comprising:
an anchorage region implantable in the femur, the anchorage region including an external threaded section with a spongiosa thread, wherein a maximum diameter of the spongiosa thread defines the maximum diameter of the shaft, the anchorage region having an anchorage region axis and a maximum radial extent with respect to the anchorage region axis;
a head region including a truncated conical connection element that is to reside outside the femur for being received in a conical bore in a femoral head prosthesis for connecting the truncated conical connection element to the femoral head prosthesis by administering blows to the femoral head prosthesis when the truncated conical connection element is received in the conical bore, the head region situated proximally of the anchorage region in an axial direction of the anchorage region and having a maximum radial extent with respect to the anchorage region axis that is no larger than the maximum radial extent of the anchorage region; and
a distal end disposed opposite the head region in the axial direction of the anchorage region, wherein the distal end includes a plurality of substantially axially extending recesses extending along said distal end; and a screwing instrument engagable in a complimentary manner with the plurality of substantially axially extending recesses for screwing the shaft into the femur.

43. A system in accordance with claim 42, wherein the head region is unitarily formed with the external threaded section.

44. A system in accordance with claim 43, wherein the distal end is coupled to the anchorage region with an axial segment of the distal end received in a blind bore in the anchorage region, wherein the blind bore includes an entrance into the blind bore which occurs at a distal end of the anchorage region with the blind bore terminating distally of a proximal end of the truncated conical connection element of the head region.

* * * * *

UNITED STATES PATENT AND TRADEMARK OFFICE
CERTIFICATE OF CORRECTION

PATENT NO. : 9,763,790 B2
APPLICATION NO. : 11/915251
DATED : September 19, 2017
INVENTOR(S) : Grappiolo et al.

It is certified that error appears in the above-identified patent and that said Letters Patent is hereby corrected as shown below:

On the Title Page

Item (30), in "Foreign Application Priority Data", in Column 1, Line 1, delete "05011259" and insert --05011259.8-- therefor Signed and Sealed this
First Day of May, 2018

Andrei Iancu
*Director of the United States Patent and Trademark Office*